United States Patent [19]

Atwal

[11] Patent Number: 4,650,797
[45] Date of Patent: Mar. 17, 1987

[54] SUBSTITUTED 1,5-BENZODIAZEPINE COMPOUNDS

[75] Inventor: Karnail Atwal, Cranbury, N.J.

[73] Assignee: E. R. Squibb & Sons, Inc., Princeton, N.J.

[21] Appl. No.: 886,847

[22] Filed: Jul. 18, 1986

[51] Int. Cl.⁴ ............... A61K 31/55; C07D 243/12
[52] U.S. Cl. ........................... 514/221; 540/567
[58] Field of Search ................... 540/567; 514/221

[56] References Cited

FOREIGN PATENT DOCUMENTS 41-18950 11/1966 Japan ........................... 540/567
47-29385 11/1972 Japan ........................... 540/567

OTHER PUBLICATIONS

Miyano et al., Synthesis of 3,3-Dimethyl-2,3,4,5,10,-11-hexahydro-11-phenyl-1H-dibenzo[b,e][1,-4]-diazepin-1-one, A New Tricyclic System Chem. Pharm. Bull., 20(7) 1588–1589 (1972).

Okamoto et al., "A Direct Reductive Deamination . . . " Chem. Pharm. Bull 29(4), 1165–1169 (1981).

Primary Examiner—Robert T. Bond
Attorney, Agent, or Firm—Lawrence S. Levinson; Stephen B. Davis

[57] ABSTRACT

Compounds of the formula

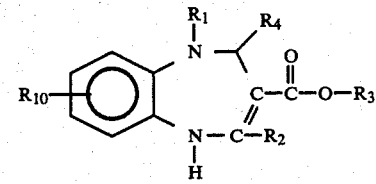

wherein $R_1$ is alkyl, alkenyl, alkynyl, cycloalkyl, or substituted alkyl, and $R_4$ is aryl or heterocyclo are disclosed. These compounds are useful as cardiovascular agents and especially as anti-hypertensive agents.

8 Claims, No Drawings

SUBSTITUTED 1,5-BENZODIAZEPINE COMPOUNDS

RELATED APPLICATIONS

The subject matter of this application is related to the 1,5-benzodiazepines disclosed in my copending U.S. application Ser. No. 762,473 filed on Aug. 5, 1985.

SUMMARY OF THE INVENTION

This invention relates to the novel substituted 1,5-benzodiazepine compounds of formula I and pharmaceutically acceptable salts thereof (I)

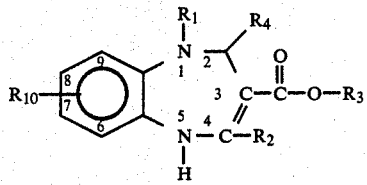

$R_1$ is lower alkyl, lower alkenyl, lower alkynyl, —(CH$_2$)$_m$-cycloalkyl, —(CH$_2$)$_n$-aryl, —(CH$_2$)$_n$-heterocyclo, —(CH$_2$)$_p$—OH, —(CH$_2$)$_p$—O-lower alkyl, —(CH$_2$)$_p$—O—(CH$_2$)$_m$-aryl, —(CH$_2$)$_p$—SH, —(CH$_2$)$_p$—S-lower alkyl, —(CH$_2$)$_p$—S—(CH$_2$)$_m$-aryl,

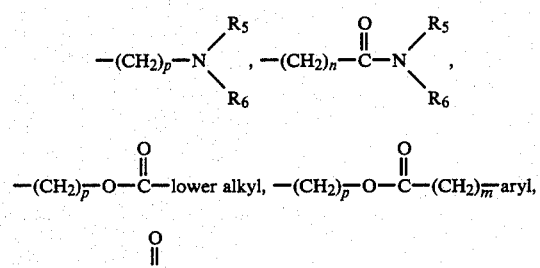

—(CH$_2$)$_n$—C(O)—O—R$_7$, halo substituted lower alkyl, or

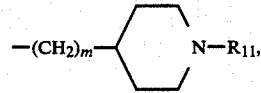

$R_2$ is hydrogen, lower alkyl, lower alkenyl, lower alkynyl, —(CH$_2$)$_m$-cycloalkyl, —(CH$_2$)$_m$-aryl, —(CH$_2$)$_m$-heterocyclo, —(CH$_2$)$_n$—OH, —(CH$_2$)$_n$—O-lower alkyl, —(CH$_2$)$_n$—O—(CH$_2$)$_m$-aryl, —(CH$_2$)$_n$—SH, —(CH$_2$)$_n$—S-lower alkyl, —(CH$_2$)$_n$—S—(CH$_2$)$_m$-aryl,

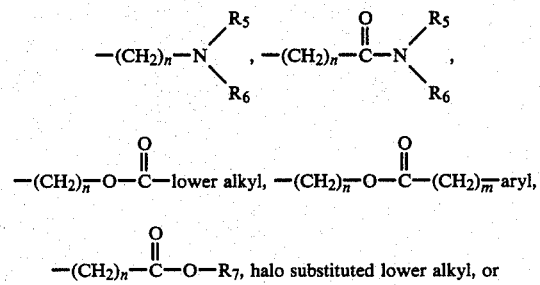

—(CH$_2$)$_n$—C(O)—O—R$_7$, halo substituted lower alkyl, or

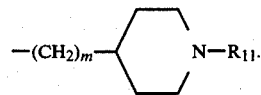

$R_3$ is hydrogen, lower alkyl, —(CH$_2$)$_m$-aryl, —(CH$_2$)$_m$-cycloalkyl, —(CH$_2$)$_n$-heterocyclo, —(CH$_2$)$_p$—OH, —(CH$_2$)$_p$—O-lower alkyl, —(CH$_2$)$_p$—O—(CH$_2$)$_m$-aryl, —(CH$_2$)$_p$—SH, —(CH$_2$)$_p$—S-lower alkyl, —(CH$_2$)$_p$—S—(CH$_2$)$_m$-aryl,

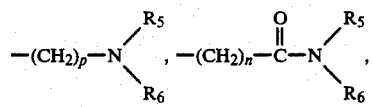

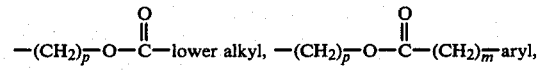

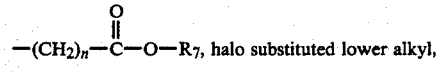

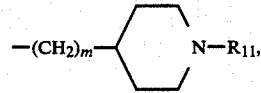

or a pharmaceutically acceptable salt forming ion.

$R_4$ is aryl or heterocyclo.

$R_5$ and $R_6$ are independently selected from the group consisting of hydrogen, lower alkyl,

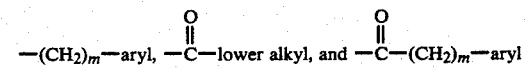

or $R_5$ and $R_6$ taken together with the N atom to which they are attached complete a heterocyclic ring of the formula

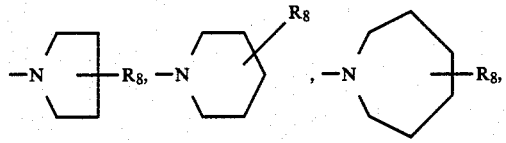

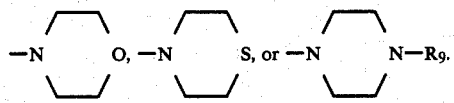

$R_7$ is hydrogen, lower alkyl, —(CH$_2$)$_m$-aryl, or a pharmaceutically acceptable salt forming ion.

$R_8$ is hydrogen, lower alkyl of 1 to 4 carbons, lower alkoxy of 1 to 4 carbons, lower alkylthio of 1 to 4 carbons, halo, CF$_3$, nitro, or hydroxy.

$R_9$ is hydrogen lower alkyl of 1 to 4 carbons,

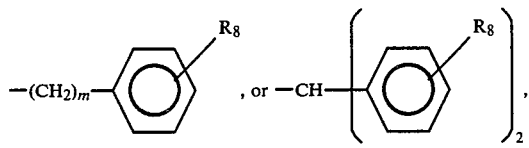

m is zero or an integer from 1 to 6.
n is an integer from 1 to 6.
p is an integer from 2 to 6.
$R_{10}$ is hydrogen, lower alkyl of 1 to 4 carbons, lower alkoxy of 1 to 4 carbons, halo, or $CF_3$.
$R_{11}$ is lower alkyl of 1 to 4 carbons,

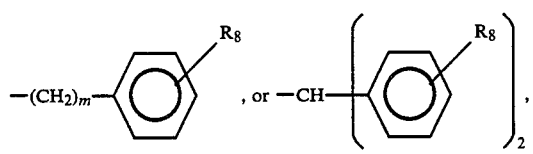

DETAILED DESCRIPTION OF THE INVENTION

This invention in its broadest aspects relates to substituted the 1,5-benzodiazepine compounds of formula I above, to compositions and the method of using such compounds as cardiovascular agents.

The term lower alkyl used in defining various symbols refers to straight or branched chain hydrocarbon radicals having up to eight carbons, preferably from one to five carbons. Similarly, the terms lower alkoxy and lower alkylthio refer to such lower alkyl groups attached to an oxygen or sulfur.

The term lower alkenyl refers to straight or branched chain hydrocarbon radicals having from two to eight carbons and one double bond, preferably three to five carbons. The term lower alkynyl refers to straight or branched chain hydrocarbon radicals having from two to eight carbons and one triple bond, preferably three to five carbons.

The term cycloalkyl refers to saturated rings of 4 to 7 carbon atoms with cyclopentyl and cyclohexyl being most preferred.

The term halo refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The term aryl refers to phenyl, 1-naphthyl, 2-naphthyl, mono substituted phenyl, 1-naphthyl, or 2-naphthyl wherein said substituent is lower alkyl of 1 to 4 carbons, lower alkylthio of 1 to 4 carbons, lower alkoxy of 1 to 4 carbons, halo, nitro, cyano, hydroxy, amino, —NH-alkyl wherein alkyl is of 1 to 4 carbons, —N(alkyl)$_2$ wherein alkyl is of 1 to 4 carbons, $CF_3$, NCS, $OCHF_2$,

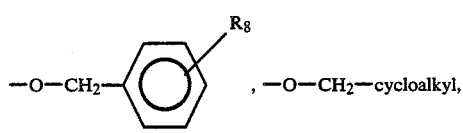

or —S—CH$_2$—cycloalkyl, and di-substituted phenyl 1-naphthyl, or 2-naphthyl wherein said substituents are selected from methyl, methoxy, methylthio, halo, $CF_3$, nitro, amino, and $OCHF_2$.

The term heterocyclo refers to fully saturated or unsaturated monocyclic rings of 5 or 6 atoms containing one to four N atoms, or one O atom and up to two N atoms, or one S atom and up to two N atoms. The monocyclic ring is attached by way of an available carbon atom. Preferred monocyclic heterocyclo groups include 2- and 3-thienyl, 2- and 3-furyl, 2-, 3- and 4-pyridinyl, and imidazolyl. The term heterocyclo also includes bicyclic rings wherein the five or six membered monocyclic ring containing O, S and N atoms as defined above is fused to a benzene ring and the bicyclic ring is attached by way of an available carbon atom in the benzene ring. Preferred bicyclic heterocyclo groups include 4, 5, 6, or 7-indolyl, 4, 5, 6, or 7-isoindolyl, 5, 6, 7 or 8-quinolinyl, 5, 6, 7 or 8-isoquinolinyl, 4, 5, 6, or 7-benzothiazolyl, 4, 5, 6 or 7-benzoxazolyl, 4, 5, 6 or 7-benzimidazolyl, 4, 5, 6 or 7-benzoxadiazolyl, and 4, 5, 6 or 7-benzofurazanyl. The term heterocyclo also includes 2-, 3-, or 4-pyridinyl rings having a substituent on one available carbon selected from lower alkyl of 1 to 4 carbons, lower alkylthio of 1 to 4 carbons, and lower alkoxy of 1 to 4 carbons, especially 2-methylthio-3-pyridinyl.

The compounds of formula I can be prepared by reacting an unsubstituted 1,5-benzodiazepine of the formula (II)

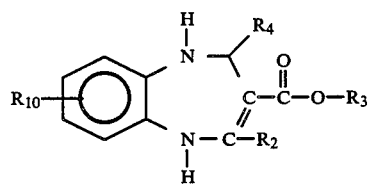

with a reagent of the formula (III)

$R_1$—L in a suitable solvent wherein L is a leaving group such as iodo, chloro, bromo, or tolylsulfonyl.

The unsubstituted 1,5-benzodiazepines of formula II can be prepared as taught in Ser. No. 762,473 noted above. For example, a 3-[(2-aminophenyl)amino]-2-alkenoic acid ester of the formula (IV)

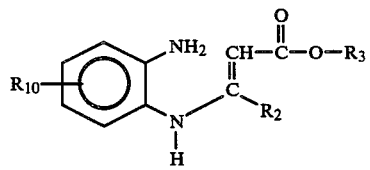

is treated in a suitable solvent with an aldehyde of the formula (V)

R₄CHO in the presence of acetic acid.

The intermediate of formula IV is prepared by treating 1,2-benzenediamine of the formula (VI)

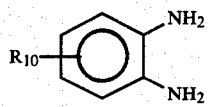

with the β-keto ester of the formula (VII)

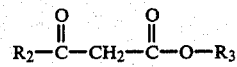

in a suitable solvent in the presence of acetic acid and heat.

If any of $R_1$, $R_2$, $R_3$, $R_4$, $R_5$ and $R_6$ in the above reactions are aryl, —$(CH_2)_n$-aryl or —$(CH_2)_m$-aryl wherein aryl is phenyl, 1-naphthyl or 2-naphthyl substituted with one or more hydroxy or amino groups, heterocyclo or —$(CH_2)_n$-heterocyclo wherein the heterocyclo ring contains an NH such as imidazolyl, or a substituted alkyl such as —$(CH_2)_n$—OH, —$(CH_2)_p$—OH, —$(CH_2)_p$—NH_2, —$(CH_2)_n$—SH, —$(CH_2)_p$—SH, or

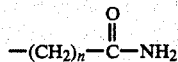

then the hydroxyl, amino, or mercaptan function should be protected during the reaction. Suitable protecting groups include benzyloxycarbonyl, t-butoxycarbonyl, benzyl, benzhydryl, etc. The protecting group is removed by hydrogenation, treatment with acid, or by other known means following completion of the reaction.

Preferred compounds of this invention are those wherein:

$R_1$ is straight or branched chain lower alkyl of 1 to 5 carbons, lower alkenyl of 3 to 5 carbons,

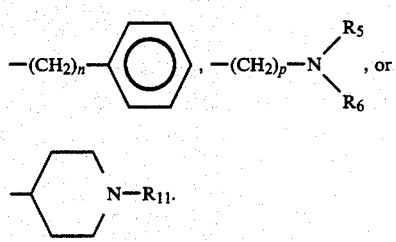

$R_2$ is straight or branched chain lower alkyl or 1 to 5 carbons, especially methyl.

$R_3$ is straight or branched chain lower alkyl of 1 to 5 carbons, benzyl,

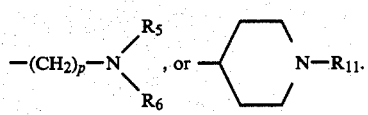

p is 2, 3, or 4.

n is 1, 2, 3 or 4.

$R_5$ and $R_6$ are independently selected from hydrogen, straight or branched chain lower alkyl of 1 to 5 carbons, and benzyl or $R_5$ and $R_6$ taken together with the N-atom to which they are attached complete a heterocyclic ring of the formula

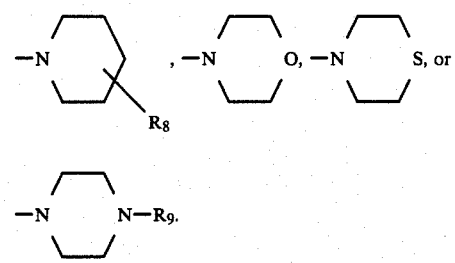

$R_4$ is mono substituted phenyl wherein said substituent is selected from lower alkyl of 1 to 4 carbons, lower alkoxy of 1 to 4 carbons, lower alkylthio of 1 to 4 carbons, halo, $CF_3$, cyano, nitro, benzyloxy, and —$OCHF_2$, disubstituted phenyl wherein said substituents are selected from methyl, methoxy, methylthio, halo, $CF_3$, and nitro, 2,3, or 4-pyridinyl, 2-methylthio-3-pyridinyl, or 2,1,3-benzoxadiazolyl.

$R_8$ is hydrogen, methyl, methoxy, methylthio, halo, $CF_3$, nitro, or hydroxy.

$R_9$ is methyl, benzyl, or diphenylmethyl.

$R_{10}$ is hydrogen, methyl, methoxy, chloro, or $CF_3$.

$R_{11}$ is benzyl or diphenylmethyl.

Most preferred are the above compounds wherein:

$R_1$ is methyl.

$R_2$ is methyl.

$R_3$ is methyl, ethyl, or isopropyl, especially ethyl.

$R_4$ is 2-nitrophenyl, 3-nitrophenyl, 2-(trifluoromethyl)phenyl, 3-(trifluoromethyl)phenyl, 2-chlorophenyl, 3-chlorophenyl, 2,3,-dichlorophenyl, 2-chloro-3-nitrophenyl, or 4-(2,1,3-benzoxadiazol)-yl, especially 3-nitrophenyl.

$R_{10}$ is hydrogen.

The compounds of formula I which contain basic amino groups form salts with a variety of inorganic and organic acids. The non-toxic pharmaceutically acceptable salts are preferred, although other salts may also be useful in isolating or purifying the product. Such pharmaceutically acceptable salts include those formed with hydrochloric acid, methanesulfonic acid, sulfuric acid, acetic acid, maleic acid, etc. The salts are obtained by reacting the product with an equivalent amount of the acid in a medium in which the salt precipitates.

In addition, the compounds of formula I in which $R_1$, $R_2$, or $R_3$ is

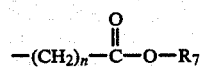

or in which $R_3$ is hydrogen include carboxylic acid salts, i.e., $R_3$ or $R_7$ is a pharmaceutically acceptable salt forming ion. Preferred salt forming ions include alkali metal salt ions such as sodium, potassium and lithium, and alkaline earth metal salt ions such as calcium and magnesium.

The compounds of formula I and the pharmaceutically acceptable salts thereof are useful as cardiovascular agents. These compounds act as calcium entry blocking vasodilators and are especially useful as antihypertensive agents. Thus, by the administration of a composition containing one (or a combination) of the compounds of this invention the blood pressure of a hypertensive mammalian (e.g., human) host is reduced. A single dose, or preferably two to four divided daily doses, provided on a basis of about 0.1 to 100 mg. per kilogram of body weight per day, preferably from about 1 to about 50 mg. per kilogram per day, is appropriate to reduce blood pressure. The substance is preferably administered orally, but parenteral routes such as the subcutaneous, intramuscular, or intravenous routes can also be employed.

As a result of the calcium entry blocking activity of the compounds of formula I, it is believed that such compounds in addition to being anti-hypertensives may also be useful as anti-arrhythmic agents, as anti-anginal agents, as anti-fibrillatory agents, as anti-asthmatic agents, and in limiting myocardial infarction.

The compounds of this invention can also be formulated in combination with a diuretic, or a beta-adrenergic agent, or angiotensin converting enzyme inhibitor. Suitable diuretics include the thiazide diuretics such as hydrochlorothiazide and bendroflumethiazide, suitable beta-adrenergic agents include nadolol, and suitable angiotensin converting enzyme inhibitors include captopril.

The compounds of formula I can be formulated for use in the reduction of blood pressure in compositions such as tablets, capsules or elixirs for oral administration, or in sterile solutions or suspensions for parenteral administration. About 10 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are illustrative of the invention. Temperatures are given in degrees centigrade.

EXAMPLE 1

2,5-Dihydro-1,4-dimethyl-2-(3-nitrophenyl)-1H-1,5-benzodiazepine-3-carboxylic acid, ethyl ester (a) 3-[(2-Aminophenyl)amino]-2-butenoic acid, ethyl ester A solution containing 1,2-benzenediamine (16.2 g., 15.0 mmole), ethylacetoacetate (19.5 g., 15.0 mmole), and acetic acid (0.6 ml.) in benzene (125 ml.) is heated at reflux temperature for 2 hours using a water separator. The reaction is allowed to cool down to room temperature and the solvent is stripped off. The residue is crystallized from isopropyl ether-hexanes to give 19.5 g. of dull white solid 3-[(2-aminophenyl)amino]-2-butenoic acid, ethyl ester; m.p. 73°–81°.

(b) 2,5-Dihydro-4-methyl-2-(3-nitrophenyl)-1H-1,5-benzodiazepine-3-carboxylic acid, ethyl ester A solution of 3-[(2-aminophenyl)amino]-2-butenoic acid, ethyl ester (5.0 g., 22.7 mmole) in absolute ethanol (30 ml.) is treated with 3-nitrobenzaldehyde (3.43 g., 22.7 mmole) and acetic acid (0.25 ml.). The reaction is allowed to stir under argon at room temperature for 24 hours. The solvent is evaporated and the residue is purified by flash chromatography (35% ethanol in hexanes). The product is crystallized from dichloromethaneisopropyl ether to give 3.51 g. of orange solid 2,5-dihydro-4-methyl-2-(3-nitrophenyl)-1H-1,5-benzodiazepine-3-carboxylic acid, ethyl ester, m.p. 147.5°–150°. TLC (silica gel; ethyl acetate: hexanes, 1:1) $R_f = 0.35$.

Anal. calc'd. for $C_{19}H_{19}N_3O_4$: C, 64.57; H, 5.41; N, 11.89 Found: C, 64.37; H, 5.38; N, 11.63.

(c) 2,5-Dihydro-1,4-dimethyl-2-(3-nitrophenyl)-1H-1,5-benzodiazepine-3-carboxylic acid, ethyl ester A reaction mixture containing 2,5-dihydro-4-methyl-2-(3-nitrophenyl)-1H-1,5-benzodiazepine-3-carboxylic acid, ethyl ester (1,5 g., 4.25 mmole) in dry dimethylformamide (5 ml.) is treated with methyl iodide (581 mg., 5.5 mmole) and then allowed to stir at room temperature for 24 hours. The reaction mixture is diluted with ethyl acetate and is washed with sodium bicarbonate, water, and brine. After drying over magnesium sulfate, the solvent is evaporated and the residue is purified by flash chromatography on silica gel (30% ethyl acetate in hexanes). The yellow foam obtained (701 mg.) is crystallized from ether-hexanes to provide yellow crystalline 2,5-dihydro-1,4-dimethyl-2-(3-nitrophenyl)-1H-1,5-benzodiazepine-3-carboxylic acid, ethyl ester; m.p. 113°–115.5°. TLC (silica gel; ethyl acetate:-hexanes, 1:1) $R_f = 0.5$.

Anal. calcd. for $C_{20}H_{21}N_3O_4$: C, 65.38; H, 5.76; N, 11.43. Found: C, 65.42; H, 5.86; N, 11.38.

EXAMPLES 2–35

Following the procedure of Example 1 the following compounds within the scope of this invention can be prepared:

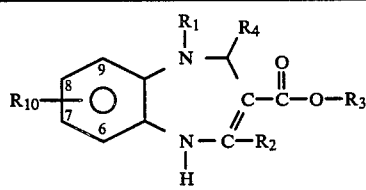

| Example | R1 | R2 | R3 | R4 | R10 |
|---|---|---|---|---|---|
| 2 | —CH2—⟨phenyl⟩ | —CH3 | —C2H5 | ⟨phenyl⟩—NO2 | —H |

-continued

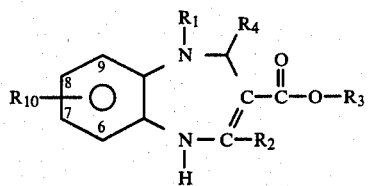

| Example | R₁ | R₂ | R₃ | R₄ | R₁₀ |
|---|---|---|---|---|---|
| 3 | $-(CH_2)_2-N(CH_3)_2$ | $-CH_3$ | $-C_2H_5$ | 4-chlorophenyl | $-H$ |
| 4 | $-(CH_2)_2-N(CH_3)-CH_2-C_6H_5$ | $-CH_3$ | $-C_2H_5$ | 2,3-dichlorophenyl | $-H$ |
| 5 | $-CH_2CH=CH_2$ | $-CH_3$ | $-C_2H_5$ | 2-(trifluoromethyl)phenyl | $-Cl$ (8-position) |
| 6 | $-(CH_2)_3-N(CH_3)-CH_2-C_6H_5$ | $-CH_3$ | $-CH(CH_3)_2$ | 3-nitrophenyl | $-H$ |
| 7 | $-CH_3$ | $-CH_3$ | $-C_2H_5$ | 2-nitrophenyl | $-H$ |
| 8 | $-(CH_2)_2-N$(thiomorpholino) | $-CH_3$ | $-CH(CH_3)_2$ | 3-nitrophenyl | $-CH_3$ (8-position) |
| 9 | $-(CH_2)_2-CH_3$ | $-CH_3$ | $-C_2H_5$ | benzofurazanyl | $-H$ |
| 10 | $-C_2H_5$ | $-CH_2$ | $-C_2H_5$ | 2-(methylthio)pyridin-3-yl | $-H$ |
| 11 | $-CH_2$-(pyridin-4-yl) | $-C_2H_5$ | $-CH(CH_3)_2$ | 4-chlorophenyl | $-H$ |

-continued

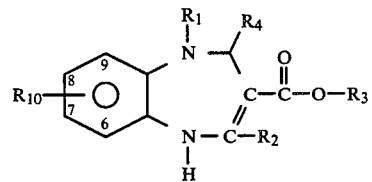

| Example | R₁ | R₂ | R₃ | R₄ | R₁₀ |
|---|---|---|---|---|---|
| 12 | 4-(N-benzyl)piperidinyl | $-CH_3$ | $-C_2H_5$ | 3-chloro-2-nitrophenyl | $-H$ |
| 13 | 4-(N-benzhydryl)piperidinyl | $-CH_3$ | $-CH(CH_3)_2$ | 4-cyanophenyl | $-Cl$ (7-position) |
| 14 | $-(CH_2)_2-N(4\text{-methylpiperazinyl})$ | $-CH_3$ | $-CH_2-C_6H_5$ | 6-nitronaphth-2-yl | $-H$ |
| 15 | $-(CH_2)_3-N(4\text{-benzylpiperazinyl})$ | $-CH_3$ | $-CH_3$ | imidazol-4-yl | $-CF_3$ (7-position) |
| 16 | $-(CH_2)_4-C_6H_5$ | $-CH_3$ | $-(CH_2)_2-O-CH_3$ | indol-3-yl | $-H$ |
| 17 | $-(CH_2)_3-(4\text{-chlorophenyl})$ | $-CH_3$ | $-(CH_2)_2-O-CH_2-C_6H_5$ | isoindol-1-yl | $-H$ |
| 18 | $-CH(CH_3)_2$ | $-CH_3$ | $-(CH_2)_2-N(CH_3)_2$ | quinolin-4-yl | $-H$ |
| 19 | $-CH_3$ | $-CH_3$ | $-(CH_2)_2-N(CH_3)-CH_2-C_6H_5$ | benzothiophen-2-yl | $-H$ |
| 20 | $-CH_3$ | $-CH_3$ | 4-(N-benzyl)piperidinyl | benzoxazol-2-yl | $-H$ |

-continued

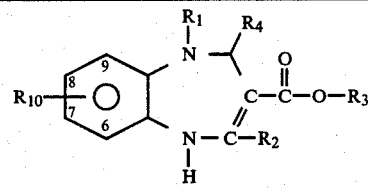

| Example | R₁ | R₂ | R₃ | R₄ | R₁₀ |
|---|---|---|---|---|---|
| 21 | −CH₂−(phenyl) | −CH₃ | −(CH₂)₃−N(morpholino) | benzimidazol-yl (NH) | −H |
| 22 | −CH₂−(2-naphthyl) | −CH₃ | −(CH₂)₂−N(piperazinyl)N−CH₃ | benzo[1,2,3]oxadiazolyl | −H |
| 23 | −CH₂CCl₃ | −CH₃ | −C₂H₅ | 4-CF₃-phenyl | −H |
| 24 | −CH₂−(cyclohexyl) | −CH₃ | −CH₂−(phenyl) | 2-NO₂-phenyl | −H |
| 25 | −(CH₂)₂−OH | −CH₃ | −C₂H₅ | 4-NO₂-phenyl | −CH₃ (7-position) |
| 26 | −(CH₂)₂−O−CH₃ | −CH₃ | −C₂H₅ | 3-Cl-phenyl | −H |
| 27 | −(CH₂)₂−O−CH₂−(phenyl) | −CH₃ | −C₂H₅ | 3,4-diCl-phenyl | −H |
| 28 | −(CH₂)₃−SH | −CH₃ | −CH₃ | 4-Cl-phenyl | −H |
| 29 | −(CH₂)₂−S−CH₃ | −CH₃ | −C₂H₅ | 3-CF₃-phenyl | −H |
| 30 | −(CH₂)₂−S−CH₂−(phenyl) | −CH₃ | −CH(CH₃)₂ | 4-CF₃-phenyl | −H |

-continued

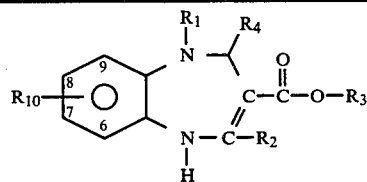

| Example | R₁ | R₂ | R₃ | R₄ | R₁₀ |
|---|---|---|---|---|---|
| 31 | $-CH_2-\overset{O}{\underset{\|}{C}}-N(CH_3)_2$ | $-CH_3$ | $-C_2H_5$ | phenyl-NO₂ | $-H$ |
| 32 | $-(CH_2)_2-O-\overset{O}{\underset{\|}{C}}-CH_3$ | $-CH_3$ | $-C_2H_5$ | phenyl-Cl,NO₂ | $-H$ |
| 33 | $-(CH_2)_2-O-\overset{O}{\underset{\|}{C}}-CH_2-$phenyl | $-CH_3$ | $-C_2H_5$ | pyridyl-SCH₃ | $-H$ |
| 34 | $-CH_2-\overset{O}{\underset{\|}{C}}-O-C_2H_5$ | $-CH_3$ | $-C_2H_5$ | phenyl-NO₂ | $-H$ |
| 35 | $-(CH_2)_2-\overset{O}{\underset{\|}{C}}-O-CH_2-$phenyl | $-CH_3$ | $-C_2H_5$ | phenyl-CF₃ | $-H$ |

EXAMPLE 36

1000 tablets each containing the following ingredients:

| | |
|---|---|
| 2,5-Dihydro-1,4-dimethyl-2-(3-nitrophenyl)-H—1,5-benzodiazepine-3-carboxylic acid, ethyl ester | 100 mg. |
| Cornstarch | 50 mg. |
| Gelatin | 7.5 mg. |
| Avicel (microcrystalline cellulose) | 25 mg. |
| Magnesium stearate | 2.5 mg. |
| | 185 mg. | are prepared from sufficient bulk quantities by mixing the product of Example 1 and cornstarch with an aqueous solution of the gelatin. The mixture is dried and ground to a fine powder. The Avicel and then the magnesium stearate are admixed with granulation. This mixture is then compressed in a tablet press to form 1000 tablets each containing 100 mg. of active ingredient.

In a similar manner, tablets containing 100 mg. of the product of any of Examples 2 to 35 can be prepared.

A similar procedure can be employed to form tablets containing 50 mg. of active ingredient.

EXAMPLE 37

An injectable solution is prepared as follows:

| | |
|---|---|
| 2,5-Dihydro-1,4-dimethyl-2-(3-nitrophenyl)-1H—1,5-benzodiazepine-3-carboxylic acid, ethyl ester | 500 g. |
| Methyl paraben | 5 g. |
| Propyl paraben | 1 g. |
| Sodium chloride | 25 g. |
| Water for injection | 5 l. |

The active substance, preservatives, and sodium chloride are dissolved in 3 liters of water for injection and then the volume is brought up to 5 liters. The solution is filtered through a sterile filter and aseptically filled into presterilized vials which are closed with presterilized rubber closures. Each vial contains 5 ml. of solution in a concentration of 100 mg. of active ingredient per ml. of solution for injection.

In a similar manner, an injectable solution containing 100 mg. of active ingredient per ml. of solution can be prepared for the product of any of Examples 2 to 35.

EXAMPLE 38

1000 tablets each containing the following ingredients:

| | |
|---|---|
| 2,5-Dihydro-1,4-dimethyl-2-(3-nitrophenyl)-1H—1,5-benzodiazepine-3-carboxylic acid, ethyl ester | 100 mg. |
| Avicel | 100 mg. |
| Hydrochlorothiazide | 12.5 mg. |
| Lactose | 113 mg. |
| Cornstarch | 17.5 mg. |
| Stearic acid | 7 mg. |
| | 350 mg. | are prepared from sufficient bulk quantities of the product of Example 1, Avicel, and a portion of the stearic acid. The slugs are ground and passed through a #2 screen, then mixed with the hydrochlorothiazide, lactose, cornstarch, and remainder of the stearic acid. The mixture is compressed into 350 mg. capsule shaped tablets in a tablet press. The tablets are scored for dividing in half.

In a similar manner, tablets can be prepared containing 100 mg. of the product of any of Examples 2 to 35.

What is claimed is:
1. A compound of the formula

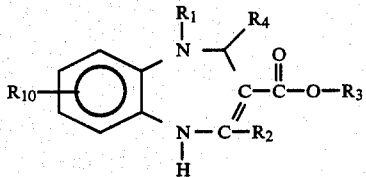

including a pharmaceutically acceptable salt thereof wherein:

$R_1$ is lower alkyl, lower alkenyl, lower alkynyl, —$(CH_2)_m$-cycloalkyl, —$(CH_2)_n$-aryl, —$(CH_2)_n$-heterocyclo, —$(CH_2)_p$—OH, —$(CH_2)_p$—O-lower alkyl, —$(CH_2)_p$—O—$(CH_2)_m$-aryl, —$(CH_2)_p$—SH, —$(CH_2)_p$—S-lower alkyl, —$(CH_2)_p$—S—$(CH_2)_m$-aryl,

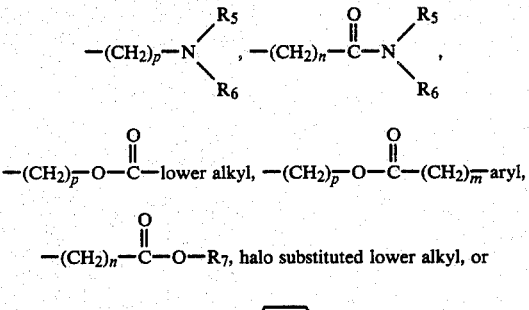

$R_2$ is hydrogen, lower alkyl, lower alkenyl, lower alkynyl, —$(CH_2)_m$-cycloalkyl, —$(CH_2)_m$-aryl, —$(CH_2)_m$-heterocyclo, —$(CH_2)_n$—OH, —$(CH_2)_n$—O-lower alkyl, —$(CH_2)_n$—O—$(CH_2)_m$-aryl, —$(CH_2)_n$—SH, —$(CH_2)_n$—S-lower alkyl, —$(CH_2)_n$—S—$(CH_2)_m$-aryl,

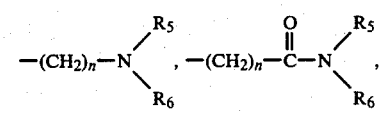

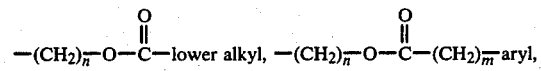

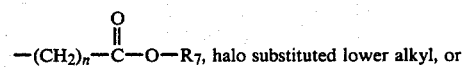

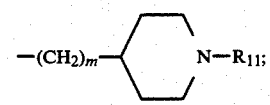

$R_3$ is hydrogen, lower alkyl, —$(CH_2)_m$-aryl, —$(CH_2)_m$-cycloalkyl, —$(CH_2)_n$-heterocyclo, —$(CH_2)_p$—OH, —$(CH_2)_p$—O-lower alkyl, —$(CH_2)_p$—O—$(CH_2)_m$-aryl, —$(CH_2)_p$—SH, —$(CH_2)_p$—S-lower alkyl, —$(CH_2)_p$—S—$(CH_2)_m$-aryl,

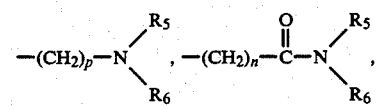

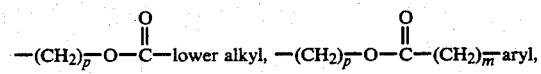

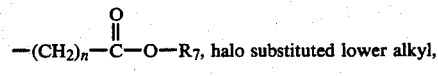

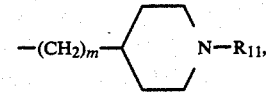

pharmaceutically acceptable salt forming ion;
$R_4$ is aryl or heterocyclo;
$R_5$ and $R_6$ are independently selected from the group consisting of hydrogen, lower alkyl,

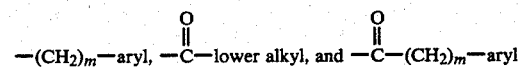

or $R_5$ and $R_6$ taken together with the N atom to which they are attached complete a heterocyclic ring of the formula

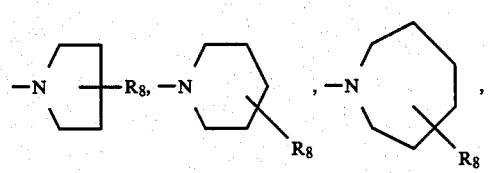

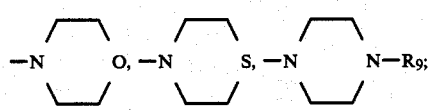

$R_7$ is hydrogen, lower alkyl, —$(CH_2)_m$-aryl, or a pharmaceutically acceptable salt forming ion;

R$_8$ is hydrogen, lower alkyl of 1 to 4 carbons, lower alkoxy of 1 to 4 carbons, lower alkylthio of 1 to 4 carbons, halo, CF$_3$, nitro, or hydroxy;

R$_9$ is hydrogen, lower alkyl,

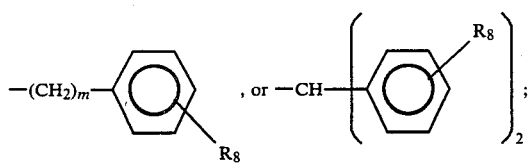

R$_{10}$ is hydrogen, lower alkyl of 1 to 4 carbons, lower alkoxy of 1 to 4 carbons, halo, or CF$_3$;

R$_{11}$ is lower alkyl of 1 to 4 carbons,

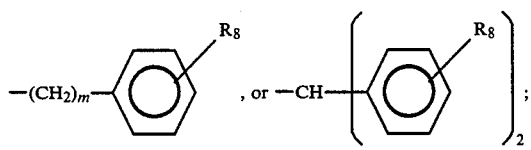

m is zero or an integer from 1 to 6;
n is an integer from 1 to 6;
p is an integer from 2 to 6;
the term "lower alkyl" refers to straight or branched chain hydrocarbon radicals of one to eight carbons;
the term "lower alkenyl" refers to straight or branched chain hydrocarbon radicals of two to eight carbons with one double bond;
the term "lower alkynyl" refers to straight or branched chain hydrocarbon radicals of two to eight carbons with one triple bond;
the term "cycloalkyl" refers to saturated rings of 4 to 7 carbons;
the term "halo" refers to chloro, bromo, and fluoro;
the term "aryl" refers to phenyl, 1-naphthyl, 2-naphthyl, mono substituted phenyl, 1-naphthyl or 2-naphthyl wherein said substituent is lower alkyl to 1 to 4 carbons, lower alkoxy of 1 to 4 carbons, lower alkylthio of 1 to 4 carbons, halo, nitro, cyano, hydroxy, amino, —NH-alkyl wherein alkyl is of 1 to 4 carbons, —N(alkyl)$_2$ wherein alkyl is of 1 to 4 carbons, —CF$_3$, —NCS, —OCHF$_2$ —O—CH$_2$—⬡—R$_8$ , —O—CH$_2$—cycloalkyl,

—S—CH$_2$—⬡—R$_8$ or —S—CH$_2$—cycloalkyl, and di-substituted phenyl, 1-naphthyl, or 2-naphthyl wherein said substituents are selected from the group consisting of methyl, methoxy, methylthio, halo, CF$_3$, nitro, amino, and OCHF$_2$; and the term "heterocyclo" refers to fully saturated or unsaturated monocyclic rings of 5 or 6 atoms containing one to four N-atoms, or one O atom and up to two N atoms, or one S atom and up to two N atoms, bicyclic rings wherein the above defined monocyclic ring is fused to a benzene ring, and substituted or unsubstituted 2-, 3- or 4-pyridinyl wherein said substituent is lower alkyl of 1 to 4 carbons, lower alkoxy of 1 to 4 carbons, and lower alkylthio of 1 to 4 carbons, said monocyclic ring attached by way of an available carbon atom and said bicyclic ring attached by way of an available carbon atom in said benzene ring.

2. A compound of claim 1 wherein:
the term "aryl" refers to phenyl, mono substituted phenyl wherein said substituent is lower alkyl of 1 to 4 carbons, lower alkoxy of 1 to 4 carbons, lower alkylthio of 1 to 4 carbons, halo, nitro, cyano, hydroxy, amino, —NH-alkyl wherein alkyl is of 1 to 4 carbons, —N(alkyl)$_2$ wherein alkyl is of 1 to 4 carbons, CF$_3$, —OCHF$_2$, or

—O—CH$_2$—⬡, and di-substituted phenyl wherein said substituents are selected from the group consisting of methyl, methoxy, methylthio, halo, —CF$_3$, nitro, amino, and —OCHF$_2$; and the term "heterocyclo" refers to 2- or 3-thienyl, 2- or 3-furyl, 2-, 3- or 4-pyridinyl, imidazolyl, 4-, 5-, 6-, or 7-indolyl, 4-, 5-, 6-, or 7-isoindolyl, 5-, 6-, 7-, or 8-quinolinyl, 5-, 6-, 7-, or 8-isoquinolinyl, 4-, 5-, 6-, or 7-benzothiazolyl, 4-, 5-, 6-, or 7-benzoxazolyl, 4-, 5-, 6- or 7-benzimidazolyl, 4-, 5-, 6-, or 7-benzoxadiazolyl, 4-, 5-, 6-, or 7-benzofuranyl, and substituted 2-, 3- or 4-pyridinyl wherein said substituent is methyl, methoxy, or methylthio.

3. A compound of claim 2 wherein
R$_1$ is straight or branched chain lower alkyl of 1 to 5 carbons, lower alkenyl of 3 to 5 carbons,

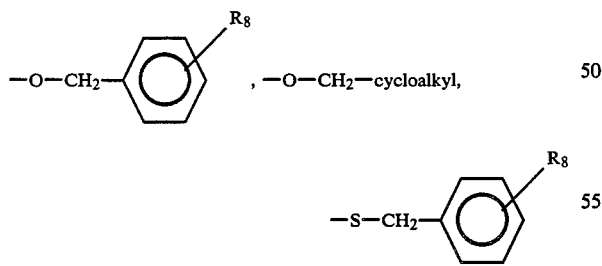

R$_2$ is straight or branched chain lower alkyl of 1 to 5 carbons;

R$_3$ is straight or branched chain lower alkyl of 1 to 5 carbons, benzyl,

—(CH$_2$)$_p$—N(R$_5$)(R$_6$) , or —⬡N—R$_{11}$;

R$_4$ is mono substituted phenyl wherein said substituent is lower alkyl of 1 to 4 carbons, lower alkoxy of 1 to 4 carbons, lower alkylthio of 1 to 4 carbons, halo, —CF$_3$, cyano, nitro, benzyloxy, and —OCHF$_2$, disubstituted phenyl wherein said substituents are selected from the group consisting of methyl, methoxy, methylthio, halo, —CF$_3$, and nitro, 2-, 3-, or 4-pyridinyl, 2-methylthio-3-pyridinyl, or 2,1,3-benzoxadiazolyl;
n is 1, 2, 3 or 4;
p is 2, 3, or 4;
$R_5$ and $R_6$ are independently selected from the group consisting of hydrogen, straight or branched chain lower alkyl of 1 to 5 carbons, and benzyl or $R_5$ and $R_6$ taken together with the N atom to which they are attached complete a heterocyclic ring of the formula

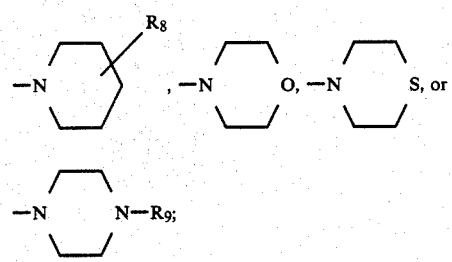

$R_8$ is hydrogen, methyl, methoxy, methylthio, halo, $CF_3$, nitro, or hydroxy;
$R_9$ is methyl, benzyl, or diphenylmethyl;
$R_{10}$ is hydrogen, methyl, methoxy, chloro, or $CF_3$; and
$R_{11}$ is benzyl or diphenylmethyl.
4. A compound of claim 3 wherein $R_2$ is methyl.
5. A compound of claim 4 wherein:
$R_1$ is methyl;
$R_3$ is methyl, ethyl or isopropyl;
$R_4$ is 2-nitrophenyl, 3-nitrophenyl, 2-chlorophenyl, 3-chlorophenyl, 2-(trifluoromethyl)phenyl, 3-(trifluoromethyl)phenyl, 2,3-dichlorophenyl, 2-chloro-3-nitrophenyl, or 4-(2,1,3-benzoxadiazol)-yl; and
$R_{10}$ is hydrogen.
6. The compound of claim 5 wherein:
$R_3$ is ethyl; and
$R_4$ is 3-nitrophenyl.
7. A composition useful in reducing blood pressure in a mammal comprising a pharmaceutically acceptable carrier and an anti-hypertensively effective amount of a compound or pharmaceutically acceptable salt thereof of the formula

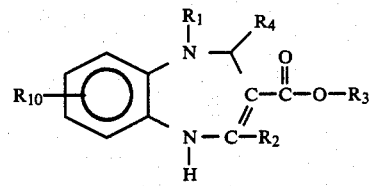

wherein $R_1$, $R_2$, $R_3$, $R_4$, and $R_{10}$ are as defined in claim 1.
8. The method of reducing blood pressure in a mammal comprising administering an effective amount of the composition of claim 7.

* * * * *